United States Patent
Burke

(10) Patent No.: US 10,945,944 B2
(45) Date of Patent: Mar. 16, 2021

(54) COMPOSITION FOR REMOVING DENTAL PLAQUE AND TARTAR

(71) Applicant: Colly A. Burke, Houston, TX (US)

(72) Inventor: Colly A. Burke, Houston, TX (US)

(*) Notice: Subject to any disclaimer, the term of this patent is extended or adjusted under 35 U.S.C. 154(b) by 391 days.

(21) Appl. No.: 15/711,510

(22) Filed: Sep. 21, 2017

(65) Prior Publication Data

US 2019/0083382 A1    Mar. 21, 2019

(51) Int. Cl.

| | | |
|---|---|---|
| *A61Q 11/00* | (2006.01) | |
| *A61K 8/19* | (2006.01) | |
| *A61K 8/34* | (2006.01) | |
| *A61K 8/22* | (2006.01) | |
| *A61K 8/92* | (2006.01) | |
| *A61K 8/9794* | (2017.01) | |
| *A61K 8/66* | (2006.01) | |
| *A61K 8/37* | (2006.01) | |
| *A61K 8/9789* | (2017.01) | |
| *A61K 8/20* | (2006.01) | |
| *A61K 8/98* | (2006.01) | |
| *A61K 8/31* | (2006.01) | |
| *A61K 8/49* | (2006.01) | |
| *A61K 8/36* | (2006.01) | |
| *A61K 8/73* | (2006.01) | |
| *A61K 8/60* | (2006.01) | |

(52) U.S. Cl.
CPC .............. *A61K 8/9794* (2017.08); *A61K 8/19* (2013.01); *A61K 8/20* (2013.01); *A61K 8/22* (2013.01); *A61K 8/31* (2013.01); *A61K 8/34* (2013.01); *A61K 8/36* (2013.01); *A61K 8/361* (2013.01); *A61K 8/37* (2013.01); *A61K 8/498* (2013.01); *A61K 8/60* (2013.01); *A61K 8/602* (2013.01); *A61K 8/66* (2013.01); *A61K 8/73* (2013.01); *A61K 8/922* (2013.01); *A61K 8/9789* (2017.08); *A61K 8/988* (2013.01); *A61Q 11/00* (2013.01); *A61K 2800/81* (2013.01)

(58) Field of Classification Search
CPC ... A61K 8/19; A61K 8/20; A61K 8/22; A61K 8/31; A61K 8/34; A61K 8/36; A61K 8/361; A61K 8/37; A61K 8/60; A61K 8/62; A61K 8/66; A61K 8/73; A61K 8/498; A61K 8/602; A61K 8/922; A61K 8/988; A61K 8/9789; A61K 8/9794; A61K 2800/81; A61Q 11/00
See application file for complete search history.

(56) References Cited

PUBLICATIONS

Shafiya Rafiq et al. "Citrus peel as a source of functional ingredient: A review." Journal of the Saudi Society of Agricultural Sciences, http://dx.doLorg/10.1016/j.jssas.2016.07.006 (2016), 8 pages.
Andrea Cespedes. "Can You Whiten Teeth with Orange Peels?" Livestrong.com, http://www.livestrong.com/article/124775-home-remedies-getting-visibly-whiter/ (accessed Jul. 18, 2017), 4 pages.
Sylvie Tremblay. "The Health Benefits of Granny Smith Apples." SFGate.com, http://healthyeating.sfgate.com/health-benefits-granny-smith-apples-3334.html (accessed Mar. 3, 2017), 4 pages.
Colly Burke, Cocorange BRITE, https://web.archive.org/web/20160220131854/http://www.cocorangebrite.com/, accessed Sep. 20, 2017, 3 pages.

*Primary Examiner* — Adam C Milligan
(74) *Attorney, Agent, or Firm* — Patterson + Sheridan, LLP

(57) ABSTRACT

The present disclosure relates to formulation for a teeth-cleaning product and a process for creating the formulation. Coconut milk and citrus pith are mixed into a formulation and heated upon a heat source until substantially boiling. Sodium bicarbonate and sodium carbonate are mixed into the formulation. Next, ethanol and hydrogen peroxide are added to the formulation. The formulation is removed from the heat source, then apple flesh and sodium chloride are added to the formulation. The formulation is allowed to cool. Next, peppermint oil and honey are added.

6 Claims, 1 Drawing Sheet

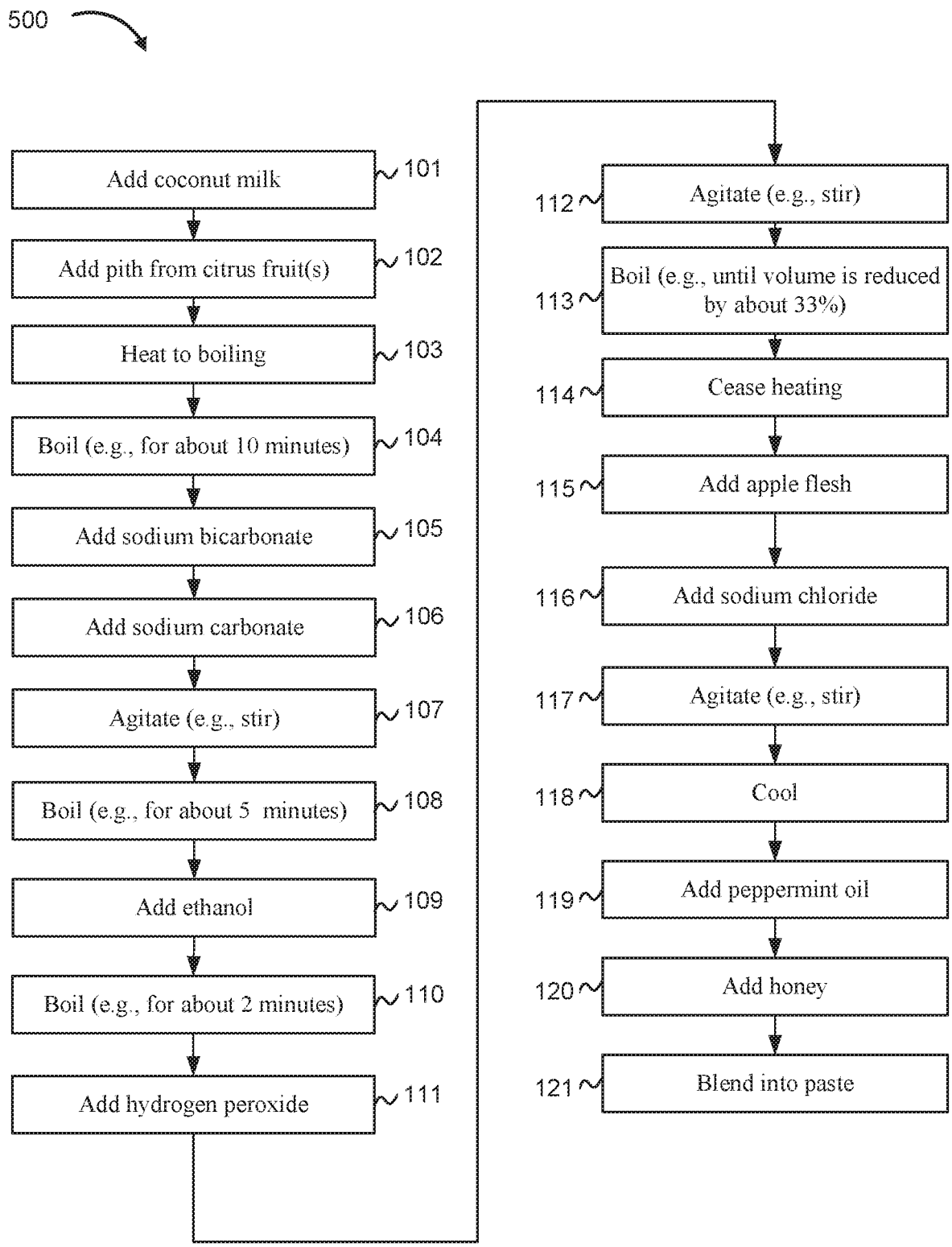

COMPOSITION FOR REMOVING DENTAL PLAQUE AND TARTAR

BACKGROUND

The American Dental Association recommends brushing at least twice per day, preferably in the morning and just before bedtime. During the day, many people have at least three meals and a few snacks. Many processed foods contain relatively high amounts salt, sugar, and carbohydrates. Such foods lower the natural pH of the mouth, thereby creating conditions that allow bacteria to multiply at an elevated rate. The human mouth is an ecosystem in which some pathogens, such as *Streptococcus mutans*, can exist and thrive without harming the hosts (i.e., humans). However, as various strains of bacteria multiply in the mouth, plaque—and eventually tartar—begin to form on the teeth, particularly around the gum line. Plaque and tartar eventually lead to tooth decay, periodontal disease, and other oral problems. For this reason, periodic removal of plaque and tartar is important for oral hygiene.

BRIEF DESCRIPTION OF THE DRAWINGS

FIG. 1 illustrates an example process for producing a formulation for cleaning teeth, according to one embodiment.

DETAILED DESCRIPTION

Embodiments presented herein provide a formulation for a teeth-cleaning product. More specifically, the present invention removes plaque and tartar from teeth.

In the following, reference is made to embodiments presented in this disclosure. However, the scope of the present disclosure is not limited to specific described embodiments. Instead, any combination of the following features and elements, whether related to different embodiments or not, is contemplated to implement and practice contemplated embodiments. Furthermore, although embodiments disclosed herein may achieve advantages over other possible solutions or over the prior art, whether or not a particular advantage is achieved by a given embodiment is not limiting of the scope of the present disclosure. Thus, the following aspects, features, embodiments, and advantages are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s). All illustrations of the drawings are for the purpose of describing selected versions of the present invention and are not intended to limit the scope of the present invention.

The tooth-cleaning formulations described herein remove plaque and tartar and also naturally whiten the teeth. These effects can typically be observed after ten days of use. Embodiments disclosed herein can be used as toothpaste (e.g., during bushing) or mouthwash (if diluted with water).

In one embodiment, a formulation for cleaning teeth comprises coconut milk, white portion of orange peel, peeled Granny Smith apple, alcohol (e.g., ethanol), sodium bicarbonate (i.e., baking soda), sodium carbonate (i.e., soda ash), hydrogen peroxide, peppermint oil, honey (e.g., raw and unfiltered), and salt (e.g., sodium chloride). The formulation can be prepared by pouring four fluid ounces (e.g., U.S. fluid ounces or imperial fluid ounces) of coconut milk into a pot along with the pith extracted from the peels of four oranges. Note that the amount of coconut milk and the amount of orange pith may vary in some embodiments. For example, in some embodiments, the amount of coconut milk ranges from one to eight fluid ounces and the amount of orange pith ranges from 20 to 250 grams.

The pot is placed on a stove burner (e.g., gas or electric) that is set on medium heat setting. Medium heat settings on different stoves can vary, but a typical burner on an electric stove will use power at a rate between 1000 Watts and 3,000 Watts (e.g., 1500 watts) on a medium setting. For a burner on a gas stove, the rate of gas consumption depends on the energy density of the type of gas used (e.g., methane, propane, etc.). A gas burner on a stove that uses methane, for example, is typically rated at between 6,000 and 25,000 British Thermal Units (BTUs). One cubic meter of methane typically produces about 35,301 BTUs when burned, so a gas burner on a medium setting will typically burn methane at a rate between 0.170 and 0.708 cubic meters of methane per hour.

Coconut milk contains medium chain saturated fatty acids (MCFAs) such as caprylic acid and capric acid. Coconut milk also contains longer chain fatty acids (LCFAs) such as myristic acid and lauric acid. The human body converts lauric acid into monolaurin, an antiviral and antibacterial compound that destroys a wide range of disease-causing organisms. Weak acids such as myristic acid, caprylic acid, and capric acids also have antibacterial properties. Coconut milk also includes zeatin, a cytokinin derived from adenine. Orange peels and other citrus rinds (e.g., containing pith or albedo) contain d-limonene, a natural solvent. D-limonene reduces smoking stains on teeth and also prevents smoking stains from developing. Citrus rinds also contain pectin, prenyloxycoumarins (e.g., auraptene, bergamottin, imperatorin, heraclenin, and oxypeucedanin), and flavonoids (e.g., hesperidin, naringin, nobiletin, and tangeretin).

The formulation is heated until boiling and allowed to boil for about ten minutes. Note that the formulation may be boiled for more or less time in other embodiments (e.g., for times ranging from one to 30 minutes). The temperature at which the formulation boils point will vary slightly as a function of the air pressure in the environment. For the purposes of this disclosure, it is assumed that the formulation is situated in an environment in which the air pressure ranges from about 860 to 1,090 millibars (mb) while the formulation boils in the pot. The formulation may be boiled for less time if the pressure is below 1013.25 mb (i.e., one atmosphere) to prevent excessive evaporation, while the formulation may be boiled for more time if the pressure exceeds 1013.25 mb to facilitate sufficient evaporation.

After the formulation has boiled for about ten minutes, about one tablespoon of sodium bicarbonate (i.e., baking soda) and about two teaspoons of sodium carbonate (i.e., soda ash or washing soda) are added to the formulation. Note that the amount of sodium bicarbonate and the amount of sodium carbonate can vary in other embodiments. For example, in some embodiments, the amount of sodium bicarbonate may range from three to 45 milliliters and the amount of sodium carbonate may range from six to 90 milliliters.

The formulation continues to boil with the burner on the medium setting while the sodium bicarbonate and sodium carbonate are stirred into the formulation. Next, the formulation is allowed to boil for about five additional minutes. Again, the boiling time can be adjusted based on the ambient pressure in which the formulation is situated. The boiling time can also vary in other embodiments (e.g., by ranging from one to fifteen minutes) even under identical ambient-pressure conditions.

Next, about one fluid ounce of ethanol is poured into the formulation. In other embodiments, the amount of ethanol may range from 0.2 fluid ounces to five fluid ounces.

The formulation is allowed to boil for about two additional minutes. Again, the boiling time can be adjusted based on the ambient pressure in which the formulation is situated. The boiling time can also vary in other embodiments (e.g., by ranging from 20 seconds to five minutes) even under identical ambient-pressure conditions.

The ethanol serves as a reagent (e.g., a weak reducing agent) in several chemical reactions that can occur within the formulation. For example, the ethanol can react with sodium bicarbonate to produce sodium carbonate, ethane, and water according to equation 1 below:

$$7C_2H_5OH + 4NaHCO_3 \rightarrow 2Na_2CO_3 + 6C_2H_6 + H_2O \quad (1)$$

Next, while the formulation is stirred, about one fluid ounce of hydrogen peroxide is gradually added to the formulation. In other embodiments, the amount of hydrogen peroxide may vary from 0.2 fluid ounces to five fluid ounces. The heat setting on the burner is reduced from medium to low and the formulation is boiled or simmered until about four fluid ounces of formulation (or, in other embodiments, 1-8 fluid ounces) remain in the pot. The pot is removed from the burner (or the burner is simply turned off).

Hydrogen peroxide is a relatively strong oxidizer and can react to some extent with the ethanol to form acetaldehyde according to equation 2 below:

$$C_2H_5OH + H_2O_2 \rightarrow CH_3CHO + 2H_2O \quad (2)$$

The acetaldehyde can react with the sodium carbonate to form sodium propanoate according to equation 3 below:

$$14CH_3CHO + 5Na_2CO_3 \rightarrow 10C_2H_5COONa + 3CO_2 + 3H_2O \quad (3)$$

Also, the hydrogen peroxide can react with the sodium carbonate to form sodium bicarbonate, carbon dioxide, and oxygen according to equation 4 below:

$$2Na_2CO_3 + 2H_2O_2 \rightarrow 2NaHCO_3 + 2CO_2 + O_2 \quad (4)$$

The ethane produced by the reaction of equation 1 can also react with the hydrogen peroxide to form carbon dioxide and water according to equation 5 below:

$$C_2H_6 + 7H_2O_2 \rightarrow 2CO_2 + 10H_2O \quad (5)$$

The ethane can also react with the oxygen gas produced by the reaction of equation 4 to form carbon dioxide and water according to equation 6 below:

$$2C_2H_6 + 7O_2 \rightarrow 4CO_2 + 6H_2O \quad (6)$$

Once the formulation is no longer being actively heated by the burner, about one half of a peeled Granny Smith apple from which the core has been removed is added to the formulation. The amount of apple can vary in other embodiments (e.g., by ranging from 20 to 150 grams). Typically, the half of the apple is sliced thin (or crushed, blended, or otherwise broken into smaller pieces) before being added to the formulation. While the formulation is still hot (e.g., at a temperature greater than about 25 degrees Celsius), about one teaspoon of sodium chloride is stirred into the formulation. The amount of sodium chloride can vary in other embodiments (e.g., by ranging from 0.1 teaspoons to three tablespoons). Next, the formulation is allowed to cool to about 23 degrees Celsius (i.e., room temperature) or a lower temperature.

Being tart, Granny Smith apples stimulate saliva production better than sweeter apple varieties. High levels of saliva decrease bacterial populations that cause cavities. Granny Smith apples are high in malic acid and also contain citric acid, oxalic acid, and tartaric acid. Granny Smith apples also contain ethyl butanoate and hexanol. If Granny Smith apples are unavailable, other tart varieties of apples (e.g., McIntosh or Honeycrisp) may be used. In this embodiment, the flesh of the apple (e.g., the pulp, the exocarp, or the hypanthium) is used rather than the skin or core of the apple. The sodium chloride is added to the mixture to prevent fermentation and lengthen the shelf life of the formulation.

Once the formulation has cooled, about two teaspoons of peppermint oil and about two teaspoons of honey (e.g., natural, raw, and unfiltered) are added to the formulation to improve the taste. The amount of peppermint oil and the amount of honey can vary in other embodiments. For example, in some embodiments, the amount of peppermint oil can range from 0.2 teaspoons to three tablespoons and the amount of honey can range from 0.2 teaspoons to three tablespoons. Finally, the formulation is blended into a paste (e.g., via a stand blender, an immersion blender, a food processor, a hand mixer, or a stand mixer).

Honey is a supersaturated sugar solution that typically comprises water, fructose, glucose, and antioxidants (e.g., catalase, ascorbic acid, flavonoids, and alkaloids). Raw honey may also comprise additional constituents such as pollen and enzymes (e.g., diastase, invertase, glucose oxidase, proteases, esterase, and β-glucosidase, plus catalase and acid phosphatase in some examples).

FIG. 1 illustrates an example process 100 for producing a formulation for cleaning teeth, according to one embodiment. To describe the process 100 in a way that accurately conveys the relative amounts of the various ingredients added to the formulation, blocks 102-121 refer to the amount of each ingredient relative to the cumulative weight of the ingredients before the process 100 is executed. Since some of the formulation evaporates during process 100 (e.g., when the formulation is boiling), the final weight of the formulation produced by process 100 is lower than the cumulative weight of the ingredients. Also, some of blocks 102-121 may be executed in an order other than the order illustrated in process 100 (for example, step 102 can be performed before step 101).

At block 101, an amount of coconut milk ranging from about 14 percent to about 50 percent by weight of the cumulative weight is added to the formulation.

At block 102, an amount of pith from one or more citrus fruits ranging from about 10 percent to about 72 percent by weight of the cumulative weight is added to the formulation. In one embodiment, a weight ratio of the amount of coconut milk to the amount of pith is about 12 to 5.

At block 103, the formulation is heated in a container (e.g., in a pot made of stainless steel, iron, ceramic titanium, borosilicate glass, soda-lime glass, or some other suitable material) via a heat source until the formulation reaches a first temperature at which the formulation is substantially boiling.

At block 104, the formulation is boiled for a first amount of time ranging from about one minute to about thirty minutes (e.g., about ten minutes). The amount of time for which the formulation is boiled may be adjusted based the on temperature and pressure conditions in the container.

At block 105, an amount of sodium bicarbonate ranging from about 2 percent to about 15 percent by weight of the cumulative weight is added to the formulation.

At block 106, an amount of sodium carbonate ranging from about 2 percent to about 15 percent by weight of the cumulative weight is added to the formulation.

At block 107, the formulation is agitated (e.g., stirred) to mix in the sodium bicarbonate and the sodium carbonate.

At block 108, the formulation is boiled for a second amount of time ranging from about one minute to about fifteen minutes (e.g., about five additional minutes or about one half of the first amount of time). Again, the amount of time for which the formulation is boiled may be adjusted based the on temperature and pressure conditions in the container.

At block 109, an amount of ethanol ranging from about 0.1 percent to about 13 percent by weight of the cumulative weight is added to the formulation. In one embodiment, a weight ratio of the amount of ethanol to the amount of sodium bicarbonate is about 96 to 100. In another embodiment, a weight ratio of the amount of ethanol to the amount of sodium bicarbonate is about 967 to 477.

Also, in one embodiment, a weight ratio of the amount of ethanol to the amount of sodium carbonate is about 645 to 530. In another embodiment, a weight ratio of the amount of ethanol to the amount of sodium carbonate is about 967 to 530.

At block 110, the formulation is boiled for a third amount of time ranging from about 20 seconds to about five minutes (e.g., about two additional minutes or about two fifths of the second amount of time). Again, the amount of time for which the formulation is boiled may be adjusted based the on temperature and pressure conditions in the container.

At block 111, an amount of hydrogen peroxide ranging from about 6 percent to about 21 percent by weight of the cumulative weight is added to the formulation. In one embodiment, a weight ratio of the amount of ethanol to the amount of hydrogen peroxide is about 13 to 10. In another embodiment, a weight ratio of the amount of ethanol to the amount of hydrogen peroxide is about 645 to 647.

Also, in one embodiment, a weight ratio of the amount of sodium carbonate to the amount of hydrogen peroxide is about 530 to 477. In another embodiment, a weight ratio of the amount of sodium carbonate to the amount of hydrogen peroxide is about 311 to 100. In another embodiment, a weight ratio of the amount of sodium carbonate to the amount of hydrogen peroxide is about 530 to 647.

At block 112, the formulation is agitated (e.g., stirred) to mix in the hydrogen peroxide.

At block 113, the formulation is boiled until a volume of the formulation is reduced by a percentage ranging from about ten percent to about 60 percent (e.g., about 30 percent). For example, if the formulation has a volume of about 6.5 fluid ounces before block 113 is executed, the formulation may be boiled until about four fluid ounces of the formulation remain.

At block 114, the heat source is no longer used to heat the formulation. For example, the container may be removed from contact with the heat source or the heat source may be deactivated.

At block 115, an amount of apple flesh ranging from about 10 percent to about 31 percent by weight of the cumulative weight is added to the formulation.

At block 116, an amount of sodium chloride ranging from about 0.8 percent to about 6 percent by weight of the cumulative weight is added to the formulation.

At block 117, the formulation is agitated (e.g., stirred) to mix in the apple flesh and the sodium chloride.

At block 118, the formulation is allowed to cool to a second temperature at least ten degrees Celsius lower than the first temperature.

At block 119, an amount of peppermint oil ranging from about 0.5 percent to about 6 percent by weight of the cumulative weight is added to the formulation.

At block 120, an amount of honey ranging from about 1 percent to about 7 percent by weight of the cumulative weight is added to the formulation.

At block 121, the formulation is blended into a paste.

As explained above, the formulation that results from process 100 will have a weight that is less than the cumulative weight of the ingredients used in process 100 because of the boiling that occurs in block 103, block 104, block 108, block 110, and block 113. In addition, the reactions described by equations 1-6 may cause some ingredients to be changed into different compounds. For this reason, the concentrations of the final constituents of the formulation may vary. However, in one embodiment, the formulation comprises: (i) caprylic acid, capric acid, myristic acid, and lauric acid (e.g., from the coconut milk); (ii) d-limonene, pectin, at least one prenyloxycoumarin, and at least one flavonoid (e.g., from the citrus pith); (iii) sodium chloride; (iv) peppermint oil; (vi) fructose, glucose, pollen, and at least one enzyme (e.g., from raw honey); and (vii) ethyl butanoate and hexanol (e.g., from a Granny Smith apple). In this example, the at least one prenyloxycoumarin may be selected from the group consisting of: auraptene, bergamottin, imperatorin, heraclenin, and oxypeucedanin. Also, the at least one flavonoid may be selected from the group consisting of: hesperidin, naringin, nobiletin, and tangeretin. In addition, the at least one enzyme may be selected from the group consisting of: diastase, invertase, glucose oxidase, proteases, esterase, and β-glucosidase, catalase, and acid phosphatase.

Note, descriptions of embodiments of the present disclosure are presented above for purposes of illustration, but embodiments of the present disclosure are not intended to be limited to any of the disclosed embodiments. Many modifications and variations will be apparent to those of ordinary skill in the art without departing from the scope and spirit of the described embodiments. The terminology used herein was chosen to best explain the principles of the embodiments or to enable others of ordinary skill in the art to understand the embodiments disclosed herein.

While the foregoing is directed to embodiments of the present disclosure, other and further embodiments of the disclosure may be devised without departing from the basic scope thereof, and the scope thereof is determined by the claims that follow.

What is claimed is:

1. A method for creating a formulation for cleaning teeth from a set of ingredients, the set of ingredients having an initial cumulative weight comprised of a sum of weight of all ingredients when initially added to create the formulation, the method comprising:

adding an amount of coconut milk ranging from 14 percent to 50 percent by weight of the initial cumulative weight to a container;

adding an amount of pith from one or more citrus fruits ranging from 10 percent to 72 percent by weight of the initial cumulative weight to the container to form a first mixture that includes the coconut milk and the pith;

heating the first mixture in the container via a heat source until the first mixture reaches a first temperature at which the first mixture is boiling;

boiling the first mixture for a first amount of time ranging from one minute to thirty minutes;

after boiling the first mixture, adding an amount of sodium bicarbonate ranging from 2 percent to 15 percent by weight of the initial cumulative weight and an amount of sodium carbonate ranging from 2 percent to 15 percent by weight of the initial cumulative weight to the container containing the first mixture to form a second mixture;

agitating the second mixture to mix in the sodium bicarbonate and the sodium carbonate;

boiling the second mixture for a second amount of time ranging from one minute to fifteen minutes;

after boiling the second mixture, adding an amount of ethanol ranging from 0.1 percent to 13 percent by weight of the initial cumulative weight to the container containing the second mixture to form a third mixture;

boiling the third mixture for a third amount of time ranging from 20 seconds to five minutes;

after boiling the third mixture, adding an amount of hydrogen peroxide ranging from 6 percent to 21 percent by weight of the initial cumulative weight to the container containing the third mixture to form a fourth mixture;

agitating the fourth mixture to mix in the hydrogen peroxide;

boiling the fourth mixture until a volume of the fourth mixture is reduced by a percentage ranging from ten percent to 60 percent;

ceasing to heat the fourth mixture via the heat source;

after boiling and then ceasing to heat the fourth mixture, adding an amount of apple flesh ranging from 10 percent to 31 percent by weight of the initial cumulative weight and an amount of sodium chloride ranging from 0.8 percent to 6 percent by weight of the initial cumulative weight to the container containing the fourth mixture to form a fifth mixture;

agitating the fifth mixture to mix in the apple flesh and the sodium chloride;

allowing the fifth mixture to cool to a second temperature at least ten degrees Celsius lower than the first temperature;

after allowing the fifth mixture to cool to the second temperature, adding an amount of peppermint oil ranging from 0.5 percent to 6 percent by weight of the initial cumulative weight and an amount of honey ranging from 1 percent to 7 percent by weight of the initial cumulative weight to the container containing the fifth mixture to form a sixth mixture; and blending the sixth mixture into a paste to form the formulation.

2. The method of claim 1, wherein the second temperature is at least 50 degrees Celsius lower than the first temperature.

3. The method of claim 1, wherein the apple flesh is from a Granny Smith apple, a McIntosh apple, or a Honeycrisp apple.

4. The method of claim 1, wherein the one or more citrus fruits include an orange, a grapefruit, a tangerine, a lemon, a lime, or a kumquat.

5. The method of claim 1, wherein the second amount of time is half of the first amount of time.

6. The method of claim 1, wherein the third amount of time is two fifths of the second amount of time.

* * * * *